United States Patent [19]
Holmes

[11] Patent Number: 6,030,606
[45] Date of Patent: Feb. 29, 2000

[54] DENTAL RESTORATIVES COMPRISING BIS-EMA6

[75] Inventor: Brian N. Holmes, St. Paul, Minn.

[73] Assignee: 3M Innovative Properties Company, St. Paul, Minn.

[21] Appl. No.: 09/102,129

[22] Filed: Jun. 22, 1998

[51] Int. Cl.$^7$ ...................................................... A61K 7/16
[52] U.S. Cl. ................................ 424/49; 522/24; 523/116
[58] Field of Search .......................... 424/49; 433/228.1; 522/8, 13, 14, 24; 523/116

[56] References Cited

U.S. PATENT DOCUMENTS

| | | | |
|---|---|---|---|
| 4,503,169 | 3/1985 | Randklev | 523/117 |
| 4,525,256 | 6/1985 | Martin | 204/159 |
| 4,674,980 | 6/1987 | Ibsen | 433/228 |
| 4,695,251 | 9/1987 | Randklev | 433/8 |
| 4,746,685 | 5/1988 | Masuhara et al. | 522/13 |
| 4,771,112 | 9/1988 | Engelbrecht . | |
| 5,034,433 | 7/1991 | Cohen et al. . | |
| 5,308,886 | 5/1994 | Masuhara | 522/81 |
| 5,332,429 | 7/1994 | Mitra | 106/35 |
| 5,362,769 | 11/1994 | Waller | 523/116 |
| 5,545,676 | 8/1996 | Palazzotto et al. | 522/15 |
| 5,575,645 | 11/1996 | Jacobs | 433/9 |
| 5,865,623 | 2/1999 | Suh | 433/228.1 |

FOREIGN PATENT DOCUMENTS

| | | |
|---|---|---|
| B-58436/86 | 12/1986 | Australia . |
| 0 102 199 | 7/1984 | European Pat. Off. . |
| 0 176 777 | 4/1986 | European Pat. Off. . |
| 0 266 548 A1 | 5/1988 | European Pat. Off. . |
| 0 315 186 A2 | 5/1989 | European Pat. Off. . |
| 63-303906 | 12/1988 | Japan . |
| WO 97/20521 | 6/1997 | WIPO . |
| WO 98/46196 | 10/1998 | WIPO . |

OTHER PUBLICATIONS

Photopolymerization Kinetics of Oligo (ethylene Oxide) and Oligo (methylene) Oxide Dimethacrylates; *Journal of Polymer Science*: Part A (vol. 31, 1053–1067)(1993).

*Primary Examiner*—Ralph Gitomer

[57] ABSTRACT

Dental restoratives comprising BisEMA6 UDMA, BisGMA and optionally TEGDMA are described. These restoratives exhibit excellent properties, including high toughness, low shrinkage, appropriate viscosity, long shelf stability, hardness and high strength.

9 Claims, No Drawings

DENTAL RESTORATIVES COMPRISING BISEMA6

FIELD OF THE INVENTION

This invention relates to dental restoratives having low shrink and high toughness physical properties. More specifically, this invention relates to dental restorative compositions comprising a specific class of ethoxylated bisphenol A methacrylate esters.

BACKGROUND OF THE INVENTION

Composites comprising polymerizable resin and filler have been widely used in dental restorations. Such composites are typically formulated from a filler dispersed in a polymerizable resin composition. Many different monomers have been used for the resin, including alkanediol acrylates or methacrylates, polyalkyleneglycol acrylates or methacrylates, bisphenol A acrylate or methacrylate esters, alkoxylated bisphenol A acrylate or methacrylate, methacrylate-terminated polyurethanes, and mixtures thereof.

SUMMARY OF THE INVENTION

Dental restorative compositions exhibiting an excellent combination of properties, including high toughness, low shrinkage, appropriate viscosity, long shelf stability, hardness and high strength have been identified. These compositions comprise the following formulation:

i) 10–30% of a resin component, which in turn comprises a) 15–45% BisEMA6, b) 15–45% UDMA, c) 10–40% BisGMA and d) 0–10% TEGDMA, and ii) 70–90% of a filler.

DETAILED DESCRIPTION OF THE PRESENT INVENTION

For purposes of the present invention, the terms "dental restorative compositions" or "dental restoratives" include both dental composites and dental cements. A composite is a highly filled paste designed to be suitable for filling substantial voids in tooth structure. Dental cements are somewhat less filled and less viscous materials than composites, and typically act as a bonding agent for additional materials, such as inlays, onlays and the like, or which act as the filling material itself if applied and cured in layers. The compositions of the present invention also find usefulness as a cured article for subsequent placement in the mouth as a prosthetic device. Examples of constructions of cured articles include crowns, bridges, inlays, onlays, implants and general formats that may be further fabricated or shaped into the desired final product for placement in the oral environment.

For purposes of the present invention, "BisEMA6" means compounds having the formula:

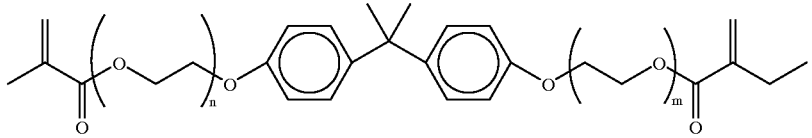

wherein m+n is between 5 and 8, and preferably (m+n) is about 6. Preferred compounds corresponding to this structure are commercially available as Sartomer CD541, (CAS number 41637-38-1).

For purposes of the present invention, BisGMA is bisphenol A diglycidyl dimethacrylate (CAS number 1565-94-2), UDMA is urethane dimethacrylate (CAS number 72869-86-4), and TEGDMA is triethylene glycol dimethacrylate (CAS number 109-16-0).

Preferred compositions include those compositions where the resin comprises a) about 30–40% BisEMA6, b) about 30–40% UDMA, c) about 20–30% BisGMA and d) about 0–10% TEGDMA. Particularly preferred compositions include those where the resin comprises a) about 33–37% BisEMA6, b) about 33–37% UDMA, c) about 23–27% BisGMA and d) about 0–5% TEGDMA.

Fillers may be selected from one or more of any material suitable for incorporation in compositions used for medical applications, such as fillers currently used in dental restorative compositions and the like. The filler is finely divided and preferably has a maximum particle diameter less than about 50 micrometers and an average particle diameter less than about 10 micrometers. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should in any event be non-toxic and suitable for use in the mouth. The filler can be radiopaque, radiolucent or non-radiopaque.

Examples of suitable inorganic fillers are naturally-occurring or synthetic materials such as quartz, nitrides (e.g., silicon nitride), glasses derived from, for example Ce, Sb, Sn, Zr, Sr, Ba or Al, colloidal silica, feldspar, borosilicate glass, kaolin, talc, titania, and zinc glass, zirconia-silica fillers; low Mohs hardness fillers such as those described in U.S. Pat. No. 4,695,251; and submicron silica particles (e.g., pyrogenic silicas such as the "Aerosil" Series "OX 50", "130", "150" and "200" silicas sold by Degussa and "Cab-O-Sil M5" silica sold by Cabot Corp.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Mixtures of these fillers are also contemplated, as well as combination fillers made from organic and inorganic materials. Fluoroaluminosilicate glass fillers, either untreated or silanol treated, may also be used. These glasses have the added benefit of releasing fluoride at the site of dental work when placed in the oral environment.

Optionally, the surface of the filler particles may be treated with a surface treatment, such as a silane coupling agent, in order to enhance the bond between the filler and the polymerizable resin. The coupling agent may be functionalized with reactive curing groups, such as acrylates, methacrylates, and the like.

The above compositions also contain materials suitable for initiating the polymerization of the resin component of the restorative. The restoratives of the present invention are cured by any appropriate means for curing free radically polymerizable systems. Preferred such systems include photoinitiator systems and redox cure (so called "chemical" cure because it may occur without exposure to light or heat) systems.

The photoinitiator should be capable of promoting free radical crosslinking of the ethylenically unsaturated moiety on exposure to light of a suitable wavelength and intensity. Visible light photoinitiators are preferred. The photoinitiator preferably is soluble in the resin composition. The photoinitiator frequently can be used alone in a one part paste light cure composition, or in combination with a peroxide containing paste in a two part chemically cured system, thereby providing a restorative having two modes of cure (a photo-initated cure and a "dark" chemically initiated cure). Alternatively, no photoinitiator need be provided, and the restorative could be provided as, for example, a chemically cured two part system.

Preferred visible light-induced initiators include camphorquinone (which typically is combined with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone, e.g., camphorquinone, and a diaryliodonium salt, e.g., diphenyliodonium chloride, bromide, iodide or hexafluorophosphate, with additional hydrogen donors (such as amines and amine alcohols).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the layer to be exposed to radiant energy, and the extinction coefficient of the photoinitiator. Typically, the photoinitiator components will be present at a total weight of about 0.01 to about 5%, more preferably from about 0.03 to about 0.1%, based on the total weight of the composition.

Restoratives of the present invention may additionally comprise adjuvants suitable for use for dental restoratives, such as colorants, flavorants, medicaments, stabilizers, viscosity modifiers, and the like. Examples of UV stabilizers include 2-(2'-hydroxy-5'-methylphenyl)-2H-benzotriazole; 2-(2'-hydroxy-5'-t-octylphenyl)-2H-benzotriazole; 2-hydroxy-4-methoxybenzophenone (UV-9); 2-(2'-hydroxy-4',6'-di-tert-pentylphenyl)-2H-benzotriazole; 2-hydroxy-4-n-octoxybenzophenone; and 2-(2'-hydroxy-5'-methacryloxyethylphenyl)-2H-benzotriazole. Such adjuvants may optionally comprise reactive functionality so that they will be copolymerized with the resin.

The following examples are given to illustrate, but not limit, the scope of this invention. Unless otherwise indicated, all parts and percentages are by weight.

Composite Materials

The following restoratives were prepared or procured for comparison purposes. Composites Ia and Ib are composites according to the present invention. Composites II–VIII are commercially available composite materials.

I. Resins and fillers were prepared for formulation as dental composite materials of the present invention as follows:

| Resin Formulation | |
| --- | --- |
| Component | Final wt % |
| Bis-GMA | 24.51% |
| Urethane Dimethacrylate | 34.32% |
| BisEMA6 (Sartomer CD541) | 34.32% |
| TEGDMA | 4.90% |
| Camphorquinone | 0.25% |
| Diphenyliodonium hexafluorphosphate | 0.50% |
| Ethylaminobenzoate | 1.00% |
| Butylated hydroxytoluene | 0.10% |
| 2-(2'-Hydroxy-5'-methylphenyl)-H-benzotriazole (Ciba-(Geigy) | 0.10% |

One hundred parts zirconia silica filler of average particle size 0.6–0.9 micrometers is mixed with deionized water at a solution temperature of between 20–30 C, and the pH is adjusted to 3–3.3 with trifluoroacetic acid (0.278 parts). A-174 silane is added to the slurry in an amount of either 10 parts or 7 parts as designated below, and the blend is mixed over 2 hours. At the end of 2 hours, the pH is neutralized with calcium hydroxide. The filler is dried, crushed and screened through a 74 or 100 micron screen.

The composites were formulated as follows:
Composite Ia
15.92% Resin Formulation
83.57% Silane Treated Filler, (10% silane treatment)
0.51% Pigments (alumina, yellow, black)
Composite Ib
16.69% Resin Formulation
82.80% Silane Treated Filler (7% silane treatment)
0.51% Pigments (Alumina, yellow, black)
II. Z100™ dental composite (3M Co.)
III. Herculite™ XRV dental composite (Kerr Co.)
IV. TPH™ dental composite (Caulk Co.)
V. Charisma™ dental composite (Kulzer)
VI. Prodigy™ dental composite (Kerr)
VII Tetric™ dental composite (Vivadent)
VIII P50™ dental composite (3M Co.)

EXAMPLE 1

Diametral Tensile Strength and Compressive Strength (CS)

Diametral tensile strength (DTS) and compressive strength (CS) measure the toughness of a dental material under strain.

For DTS and CS measurements the mixed, uncured composite samples were injected into a glass tube having a 4 mm inner diameter. The filled tube was subjected to 2.88 kg/cm$^2$ (40 psi) pressure followed by curing while under pressure, by exposure to a Visilux™ 2 (3M, St. Paul) dental curing light. The cured samples were allowed to stand for 1 hour at about 37° C., 90%+relative humidity. They were then cut on a diamond saw to form cylindrical plugs approximately 2 mm long for measurement of diametral tensile strength, and approximately 8 mm long for measurement of compressive strength. Five samples of each material were prepared for CS and ten samples were prepared for DTS. The plugs were stored in distilled water at approximately 37° C. for about 24 hours and their DTS and CS were determined according to ISO specification 7489 (or American Dental Association ("ADA") specification No. 27) using an Instron Mechanical Testing Instrument (Model 4500 Series).

| Composite | Ia | II | III | IV |
|---|---|---|---|---|
| Diametral Tensile Strength | 13547 ± 600 psi 93.5 ± 4 Mpa | 13738 ± 469 psi 94.8 ± 3 MPa | 12648 ± 545 psi 87 ± 4 MPa | 11314 ± 470 psi 78 ± 3 Mpa |
| Compressive Strength | 64907 ± 1549 psi 448 ± 11 Mpa | 62765 ± 937 psi 433 ± 6 MPa | 62306 ± 1304 psi 429 ± 9 MPa | 62512 ± 970 psi 431 ± 7 Mpa |

This example demonstrates the excellent combination of properties of the restorative of the present invention as compared to commercially available restorative materials.

EXAMPLE 2

Post Gel Shrinkage

Materials and Methods

A stacked biaxial strain gage (CEA-06-032WT-120, Micro Measurements Group, Raleigh, N.C., USA) was used to measure shrinkage strains in two perpendicular directions as a composite sample is photo-cured. The self-temperature-compensating strain gages display a flat temperature response in the temperature range for these experiments (20–40C). A strain conditioner (2101 A Series, Micro Measurements Group, Raleigh, N.C., USA) converted electrical resistance changes in the strain gage to voltage changes through a quarter-bridge circuit with an internal reference resistance. A strain output measurement cycle consisting of a 60 second light exposure and 4 additional minutes of monitoring was applied to each of the samples. The perpendicular strains were averaged since the material properties were homogeneous and isotropic on a macro scale. The intensity of the curing light source (Visilux™ 2, 3M Dental Products Division, St. Paul, Minn., USA) was 566 mW/cm2 as measured by Cure Rite Visible curing light meter (Model #8000, EFOS Inc., Williamsville, N.Y., USA)

The composite sample (25 mg) was placed on top of the strain gage, where the actual measuring surface or gage length was 0.81 mm. The curing light guide was positioned 2 mm above the sample. An electronic shutter was used to interrupt the light to the composite sample until the full curing light intensity was reached and to interrupt the light at the end of the exposure period. This eliminated the 0.5 second "warm-up" period observed as the curing light increased in intensity to its maximum. The composite samples, three replicates, were light-cured for 60 seconds. The relationship between strain and time was produced by averaging the two strains recorded by the strain gage. A mean curve was created by calculating the mean of the strain from the 3 samples at each time point. The final shrinkage was recorded as the strain 4 minutes after the light was turned off. The results were standardized to the performance of 3M Z100™ composite.

WATTS SHRINKAGE

The Watts Shrinkage (Watts) test measures shrinkage in terms of volumetric change after polymerization. A 145 mg sample of the composite is weighed out. The procedures described in *Determination of Polymerization Shrinkage Kinetics in Visible-Light-Cured Materials:Methods Development* (*Dental Materials,* October 1991, pgs 281–286) were used to prepare the samples. Three replicates were performed for each sample. The results were standardized to the performance of 3M Z100™ composite.

| SHRINKAGE | | | |
|---|---|---|---|
| | Watts | | PGS |
| VI | 1.18 | II | 1 |
| V | 1.06 | V | 0.80 |
| IV | 1.04 | IV | 0.77 |
| III | 1.02 | VI | 0.75 |
| II | 1 | III | 0.69 |
| VII | 0.85 | Ia | 0.67 |
| Ia | 0.69 | VII | 0.65 |

EXAMPLE 3

Barcol Hardness

Samples of each composite were cured in 2.5 mm thick Teflon molds sandwiched between polyester (PET) film and glass slides for 40 seconds each with a Visilux™ 2 curing light (3M). After irradiation, the PET films were removed and the hardness of the sample at the bottom of the mold was measured using a Barber-Coleman Impressor (a hand-held portable hardness tester; Model GYZJ 934-1; from Barber-Coleman Co. Industrial Instruments division, Lovas Park, Ind.) equipped with an indenter. Top and bottom Barcol hardnesses were measured at 5 minutes and at 24 hrs after light exposure.

For each composition tested, three samples were irradiated, with five readings taken at the bottom of each sample. The readings were averaged for each composition. The results were standardized to the performance of 3M Z100™ composite.

| BARCOL HARDNESS | | | |
|---|---|---|---|
| | Top | | Bottom |
| II 24 hrs | 1.04 | II 24 hrs | 1.04 |
| I 24 hrs | 1.01 | II | 1 |
| II | 1 | I 24 hrs | 0.99 |
| III 24 hrs | 0.96 | Ia | 0.96 |
| Ia | 0.96 | IV 24 hrs | 0.94 |
| IV 24 hrs | 0.95 | III 24 hrs | 0.93 |
| III | 0.92 | IV | 0.89 |
| IV | 0.90 | III | 0.87 |

EXAMPLE 4

Fracture Toughness

The fracture toughness (FT) of the composite test samples, five replicates was measured using the short rod specimen geometry as disclosed in U.S. Pat. No. 5,332,429 (the disclosure of which is hereby incorporated by reference) at column 17, line 63 to column 18, line 27. The results were standardized to the performance of 3M Z 100™ composite. The samples were stored in water for at least 48 h prior to testing.

| FRACTURE TOUGHNESS (FT) | |
|---|---|
| | FT |
| Ib | 1.11 |
| II | 1 |
| VII | 0.94 |
| IV | 0.93 |
| III | 0.91 |
| VIII | 0.82 |

I claim:

1. A dental restorative composition comprising
   i) 10–30% of a resin component, which in turn comprises
      a) 15–45% BisEMA6,
      b) 15–45% UDMA,
      c) 10–40% BisGMA and
      d) 0–10% TEGDMA; and
   ii) 70–90% of a filler.

2. The dental restorative composition of claim 1, wherein the resin comprises
   a) 30–40% BisEMA6,
   b) 30–40% UDMA,
   c) 20–30% BisGMA and
   d) 0–10% TEGDMA.

3. The dental restorative composition of claim 1, wherein the resin comprises
   a) about 33–37% BisEMA6,
   b) about 33–37% UDMA,
   c) about 23–27% BisGMA and
   d) about 0–5% TEGDMA.

4. The dental restorative composition of claim 1, wherein said composition is a dental composite.

5. The dental restorative composition of claim 1, wherein said composition is a cement.

6. The dental restorative composition of claim 1, wherein said filler is selected from the group consisting of quartz; nitrides; glasses derived from Ce, Sb, Sn, Zr, Sr, Ba or Al; colloidal silica; feldspar; borosilicate glass; kaolin; talc; titania; zinc glass; zirconia-silica; fluoroaluminosilicate glass; and mixtures thereof.

7. The dental restorative composition of claim 1, wherein said composition comprises a photoinitiator.

8. The dental restorative composition of claim 1, wherein said composition comprises a redox polymerization initiator.

9. The dental restorative composition of claim 1, wherein said composition comprises a photoinitiator and a redox polymerization initiator.

* * * * *